United States Patent [19]

Chupp

[11] 4,311,858

[45] Jan. 19, 1982

[54] PROCESS FOR PRODUCING N-(HALOMETHYL) ACYL-AMIDES

[75] Inventor: John P. Chupp, Kirkwood, Mo.

[73] Assignee: Monsanto Company, St. Louis, Mo.

[21] Appl. No.: 211,608

[22] Filed: Dec. 1, 1980

[51] Int. Cl.³ .......................................... C07C 102/00
[52] U.S. Cl. ................................. 564/214; 564/166;
564/170; 564/182; 564/193; 564/194; 564/197;
564/189; 564/190; 564/191; 564/209; 564/210;
564/211; 564/215; 564/217; 564/218; 564/223;
564/224; 564/201; 564/202; 564/203
[58] Field of Search ............... 564/214, 210, 211, 193,
564/194, 197, 166, 170, 182, 201, 202, 203, 215,
217, 218, 209, 189, 190, 191, 223, 224; 570/259

[56] References Cited

U.S. PATENT DOCUMENTS 3,637,847  1/1972  Olin ..................................... 564/214

OTHER PUBLICATIONS

Gibbs et al., J. Am. Chem. Soc., 55(1933), pp. 753–756.

Primary Examiner—Arthur P. Demers
Attorney, Agent, or Firm—William I. Andress; Howard C. Stanley

[57] ABSTRACT

The disclosure herein relates to a new process for the preparation of N-(halomethyl) acylamides by reacting the corresponding N-(alkoxymethyl) acetamide with a hydrogen halide.

25 Claims, No Drawings

PROCESS FOR PRODUCING N-(HALOMETHYL) ACYL-AMIDES

BACKGROUND OF THE INVENTION

The invention herein pertains to the field of processes for the preparation of N-(halomethyl) acylamides particularly, N-(halomethyl) acetamides.

DESCRIPTION OF THE PRIOR ART

N-(halomethyl) acylamides generally are known in the prior art. A particularly useful subclass of these compounds are the 2-haloacetamides, the preferred compounds to which the process herein is applicable. These compounds are useful as herbicides themselves or as intermediates in the production of a wide variety of other N-methylene ether substituted 2-haloacetamides as disclosed, e.g., in U.S. Pat. Nos. 3,442,945, 3,630,716, 3,637,847, 3,574,746 and 3,586,496 and German Appln. No. 2,648,008. Other prior art N-methylene ether substituted 2-haloacetamides derived from the above N-(halomethyl) intermediates include those wherein the halogen atom of the N-(halomethyl) radical is replaced by alkoxy, polyalkoxy, aryl, heterocyclyl, etc., radicals.

The primary method disclosed in the prior art for producing N-(halomethyl)-2-haloacetamides involves the reaction of a primary aromatic amine with formaldehyde to produce the corresponding phenylazomethine which is then haloacetylated to obtain the desired N-halomethyl compound as disclosed, e.g., in said U.S. Pat. Nos. 3,630,716 and 3,630,847.

Canadian Pat. No. 779,917 discloses alternative methods for producing N-(chloromethyl)-2-haloacetamides. In a first embodiment, a primary or secondary amine is reacted with formaldehyde to obtain the corresponding hexahydrotriazine which is then reacted with chloroacetyl chloride to obtain the corresponding N-(chloromethyl)-2-chloroacetamide. In a second procedure, a primary amine is reacted with chloroacetyl chloride, then with formaldehyde to produce the corresponding N-methylol-2-chloroacetamide, which, in turn, is reacted with phosphorus pentachloride to obtain the corresponding N(-chloromethyl)-2-chloroacetamide.

To the knowledge of the inventor herein, it is unknown in the prior art to prepare N-(halomethyl)-acylamides by the metathetical reaction of a hydrogen halide with an N-methylene ether substituted-acylamide as described in more detail below.

SUMMARY OF THE INVENTION

The invention herein relates to a process for preparing compounds of Formula I

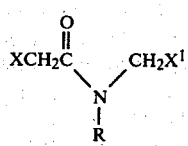   I which comprises reacting a hydrogen halide with a compound of Formula II

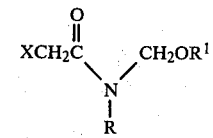   II where in the above formulae

X is hydrogen, halogen, a $C_{1-6}$ alkyl or haloalkyl radical, a $C_{3-7}$ cycloalkyl radical, a phenyl or benzyl radical or any of said radicals optionally substituted with other radicals which are inert to a hydrogen halide, e.g., halogen, $NO_2$, $CF_3$, $C_{1-6}$ alkyl or alkoxy, phenyl or benzyl, etc.;

$X^1$ is chloro, bromo or iodo;

R is an acyclic 1-alken-1-yl radical having up to 10 carbon atoms, a $C_{5-7}$ 1-cycloalken-1-yl radical, a phenyl radical or said 1-cycloalken-1-yl or phenyl radicals substituted with one or more $C_{1-6}$ alkyl, alkoxy or alkoxyalkyl, $C_{2-4}$ alkenyl or $C_{3-4}$ alkenyloxy, $NO_2$ or $CF_3$ radicals or halogen and $R^1$ is a hydrocarbyl radical having up to 10 carbon atoms or such radical substituted with halogen or $C_{1-8}$ alkoxy or alkoxyalkyl groups.

The process of this invention in preferred aspects is used to prepare compounds according to Formula I wherein X and $X^1$ are both chloro, $X^1$ being derived from a concentrated hydrogen chloride and R is substituted phenyl radical as defined above. Preferably, X and $X^1$ should always be the same halogen, because some halogen interchange can occur when different halogens are involved.

The process of this invention is suitably and preferably conducted at room temperatures or more broadly within the range of 20° to 100° C. A controlling parameter with respect to temperatures of operation is that hydrolysis of the 2-haloacetamide tends to occur as the temperature is increased. Hence, this process should be operated at temperatures which minimize hydrolysis of the acetamide.

The unique and unobvious character of the present invention is made manifest by reference to expected reactions which do not occur when N-(alkoxymethyl)-acylamides are reacted with a hydrogen halide according to this invention. For example, in starting N-(alkoxymethyl)-2-haloacetamides having alkoxy or alkoxyalkyl radicals substituted on the anilide ring, there are two ether linkages which could interchange with the reactant halide. However, according to the process of this invention, only the ether linkage in the N-methylene ether moiety is interchanged, leaving the anilide-substituted ether linkage intact.

Furthermore, the N-(alkoxymethyl)-2-haloacetamide starting materials used herein are amide animals, although for convenience they may be and are referred to as N-methylene ether-substituted 2-haloacetamides. Accordingly, it is not at all obvious or expected that a halogen-ether exchange would occur at all, since equally feasible and expected reactions could occur, e.g., cleavage could occur at the bond between the alkoxymethyl radical and the amide nitrogen atom resulting in the formation of an N-hydrogen-2-haloacetamide.

DETAILED DESCRIPTION OF THE INVENTION

The process of this invention will be exemplified in Examples 1 and 2 with respect to embodiments for preparing N-enamide compounds.

Structure proof of the products produced in the examples below was afforded by mass spectroscopy, gas liquid chromatography, nuclear magnetic resonance and/or elemental analysis.

EXAMPLE 1

Two (2.0) grams of N-(methoxymethyl)-N-[2-methyl-1-(1-methylethyl)-1-propen-1-yl]-2-chloroacetamide dissolved in 20 ml of $CCl_4$ were contacted with 20 ml of 37% HCl and shaken in a separatory funnel. When NMR analysis of lower layer indicated complete reaction, the material was vacuum stripped at about 50° C./0.05 mm Hg to give 1.6 g of product.

| Anal. calc'd for $C_{10}H_{17}Cl_2NO$ (%) | | |
|---|---|---|
| Element | Theory | Found |
| C | 50.43 | 51.17 |
| H | 7.19 | 7.39 |
| N | 5.88 | 6.07 |

The product, structure confirmed by NMR, was identified as N-(chloromethyl)-N-[2-methyl-1-(1-methylethyl)-1-propen-1-yl]1-2-chloroacetamide. NMR characteristics for this product are as follows:

($CDCl_3$) $\delta 0.95$, 1.1 CH($\underline{CH}_3$)$_2$ (2 doublets, 3H each, J=7 Hz); $\delta 2.7$, 2.84 (2 singlets, 3H each)=C($\underline{CH}_3$)$_2$; $\delta$ 3,95, ($CH_3$)$_2$$\underline{CH}$—(heptet 1H, J=7 Hz); $\delta 4.02$, Cl$\underline{CH}_2$CO (S, 2H); $\delta = 5.38$, N—$\underline{CH}_2$Cl (AB quartet, 2H, J=8.5 Hz).

EXAMPLE 2

Following the general procedure described in Example 1, 2.0 g of N-(methoxymethyl)-N-(1,2-dimethyl-1-propen-1-yl)-2-chloracetamide were dissolved in 20 ml of $CCl_4$ and shaken in a small separatory funnel with 25 ml of 37% HCl. The lower organic layer was drawn off and NMR indicated complete reaction; the solvent was stripped on a water bath (60° C.) at pump pressure to give 1.2 g (57% yield) of product.

| Anal. calc'd for $C_8H_{13}Cl_2NO$ (%) | | |
|---|---|---|
| Element | Theory | Found |
| C | 45.73 | 45.24 |
| H | 6.24 | 6.21 |
| N | 6.67 | 6.35 |

The product was identified as N-(chloromethyl)-N-(1,2-dimethyl-1-propen-1-yl)-2-chloroacetamide. Nmr characteristics for this product are as follows:

($CDCl_3$) $\delta 1.65$, 1.8, 1.95 (3=C-$\underline{CH}_3$, 9 protons, each broad singlet with partial multiplicity): $\delta = 4.0$, Cl$CH_2$ CO (singlet, 2H); $\delta = 5.35$, Cl$\underline{CH}_2$N (AB quartet, 2H, J=9 Hz).

EXAMPLE 3

The precursor N-(methoxymethyl)-N-(acyclic 1-alken-1-yl)-2-chloroacetamides used to prepare the compounds in Examples 1 and 2 are suitably prepared by an N-alkylation process of the corresponding sec-amide as disclosed in more detail in copending U.S. application Ser. No. 63,005 filed Aug. 2, 1979, now U.S. Pat. No. 4,258,196, assigned to the assignee herein. Thus, the precursor N-(alkoxymethyl) amide used in Example 2 is prepared as follows:

To 200 ml of $CH_2Cl_2$ are added 16.0 g (0.1 mol of N-(1,2-dimethyl-1-propenyl)-2-chloroacetamide, 4.0 g of benzyl triethylammonium chloride and 16 ml of bromomethyl methyl ether. The mixture is cooled to 10° C. and 100 ml of 50% NaOH added all at once. After aqueous workup, 4.0 g (19.5% yield) of the corresponding N-(methoxymethyl)-2-chloroacetamide product, b.p. 110°–120° C./0.05 (Kugelrohr), are obtained.

| Anal. calc'd for $C_9H_{16}CNO_2$ (%): | | |
|---|---|---|
| Element | Theory | Found |
| C | 52.56 | 50.65 |
| H | 7.84 | 7.56 |
| N | 6.81 | 6.38 |

In other embodiments, the process of this invention is used to prepare N-(halomethyl) acetamides further characterized by a cycloalkenyl radical also attached to the nitrogen atom; Examples 4–7 exemplify this process embodiment.

EXAMPLE 4

This example describes the preparation of an N-(chloromethyl)-N-(1-cyclohexen-1-yl)-2-haloacetamide by use of the process of this invention. Paragraph (a) describes the use of the above-mentioned N-alkylation process to prepare the precursor N-(alkoxymethyl)-2-haloacetamide used to prepare the corresponding N-(halomethyl)-2-haloacetamide and paragraph (b) describes the reaction of the amide prepared in paragraph (a) with a hydrogen halide to produce said N-halomethyl compound.

(a) This paragraph describes the use of a multiphase system to generate the anion of the desired secondary 2-haloacetamide and alkylation of said anion, preferably in the presence of a phase transfer catalyst to produce the desired corresponding tertiary 2-haloacetamide.

A mixture of 400 g of the sec-amide, N-(2,6-dimethyl-1-cyclohexen-1-yl)-2-chloroacetamide, m.p. 114°–115° C., in 760 ml methylene chloride and 300 ml chloromethyl methyl ether were mixed with 2 g benzyl triethyl ammonium bromide. The mixture was cooled to 10° C. then added in a thin stream over 0.5 hour to a vigorously stirred mixture of 1100 ml of 50% sodium hydroxide, 300 ml methylene chloride and 9 g benzyl triethyl ammonium bromide contained in a 5-liter 4-necked round bottomed flask. Exterior cooling with an ice/acetone bath was necessary to maintain the temperature under 25° C. The mixture was stirred for an additional one hour. GLC showed 78% tertiary amide produced and 22% of corresponding O-alkylated by-product, O-(methoxymethyl)-N-(2,6-dimethyl-1-cyclohexen-1-yl)-2-chloroacetimidate. The reaction mixture was separated, and the organic layer given a simple wash with 5% HCl solution to convert the imidate to starting secondary amide. To the washed mixture in methylene chloride was added an additional 120 ml of chloromethyl methyl ether and 5.0 g of the quaternary ammonium phase-transfer catalyst, followed by 350 ml of 50% NaOH with stirring. After separation of layers and additional water washing, the product was filtered through clay; methylene chloride solvent was evaporated and the residue heated to 85° C. (0.55 mm Hg), then filtered through clay to purify the product. The product was recovered in about 99% yield and had a boiling point of 127° C. (0.15 mm Hg).

| Anal. calc'd for $C_{12}H_{20}ClNO_2$ (%): | | |
| --- | --- | --- |
| Element | Theory | Found |
| C | 58.65 | 58.48 |
| H | 8.20 | 8.22 |
| N | 5.70 | 5.62 |

The product was identified as N-(2,6-dimethyl-1-cyclohexen-1-yl)-N-(methoxymethyl)-2-chloroacetamide.

The above process may be performed without imidate formation thus obviating acid-catalyzed reformation of sec-amide when lesser quantities, i.e., up to 50 g of the sec-amide are used, the catalyst concentration is increased up to 20–50% of the amount of sec-amide used and the base, NaOH, is added all at once.

(b) One (1.0) g of the product produced in paragraph (a) above was placed in 10 ml of $CCl_4$, stirred 2 hours with 10 ml of 37% HCl. After reaction had gone to completion as indicated by NMR, the formed layers were separated, 5 ml of fresh HCl added and the mixture stirred for 1 hour. After layer separation, the organic layer was vacuum stripped to 75° C./0.2 mm Hg to give 0.8 g (93% yield) of oil.

| Anal. calc'd for $C_{11}H_{18}Cl_2NO$ (%) | | |
| --- | --- | --- |
| Element | Theory | Found |
| C | 52.60 | 51.87 |
| H | 7.22 | 6.79 |
| N | 5.58 | 5.27 |

The product was identified as N-(2,6-dimethyl-1-cyclohexen-1-yl)-N-(chloromethyl)-2-chloroacetamide.

When the process of paragraph (b) is performed substituting N-(ethoxymethyl)-N-(2,6-dimethyl-1-cyclohexen-1-yl)-2-chloroacetamide as the precursor amide, the same product is obtained as identified in paragraph (b).

EXAMPLE 5

This example describes an embodiment of the invention process using hydrogen bromide as the halogenating agent.

Two (2.0) g of N-(methoxymethyl)-N-(2,6-dimethyl-1-cyclohexen-1-yl)-2-chloroacetamide in 20 ml of $CCl_4$ were shaken with 10 ml of 48% HBr. Upon shaking and standing for a period of time, Nmr analysis of the $CCl_4$ solution showed favorable reaction, i.e., about 75% complete. A second 10 ml portion of 48% HBr effected complete reaction. The lower organic layer of the solution was separated off and stripped to give 1.7 g yield after high vacuum stripping. Nmr excellent. The product crystallized on standing and was triturated with pentane to give 0.8 g yield, plus about 0.3 g from cold pentane; white solid, m.p. 52°–53° C.

| Anal. calc'd for $C_{11}H_{17}BrClNO$ (%): | | |
| --- | --- | --- |
| Element | Theory | Found |
| C | 44.84 | 44.78 |
| H | 5.82 | 5.84 |
| N | 4.75 | 4.77 |

The product was identified as N-(bromomethyl)-N-(2,6-dimethyl-1-cyclohexen-1-yl)-2-chloroacetamide.

EXAMPLE 6

N-(Methoxymethyl)-N-(2,6-diethyl-1-cyclohexen-1-yl)-2-chloroacetamide prepared from 25 g of the requisite sec-amide was dissolved in 100 ml $CCl_4$ and shaken with 600 ml 37% HCl. The layers were separated and exercise repeated once again with fresh HCl. NMR showed complete reaction. The organic layer was dried, filtered and stripped to 0.1 mm at 40° C. to give 23.5 g (78% yield from sec-amide). The oil was taken up in hexane and ppt at dry ice temperature, scratching produced solid which was filtered cold and dried in vacuum desiccator to give 17.5 g, m.p. 25°–30° C.

| Anal. calc'd for $C_{13}H_{21}Cl_2NO$ (%): | | |
| --- | --- | --- |
| Element | Theory | Found |
| C | 56.12 | 55.97 |
| H | 7.61 | 7.68 |
| N | 55.49 | 55.39 |

The product was identified as N-(chloromethyl)-N-(2,6-diethyl-1-cyclohexen-1-yl)-2-chloroacetamide.

EXAMPLE 7

Similarly prepared as in Example 6 was an isomeric mixture of the compound N-(chloromethyl)-N-(2-ethyl-6-methyl-1-cyclohexen-1-yl)-2-chloroacetamide and its N-(2-methyl-6-ethyl) isomer; $N_D^{25}$ 1.5280.

| Anal. calc'd for $C_{12}H_{19}Cl_2NO$ (%): | | |
| --- | --- | --- |
| Element | Theory | Found |
| C | 54.55 | 55.42 |
| H | 7.25 | 7.52 |
| N | 26.84 | 23.62 |

The process according to this invention is further shown to be suitable for the preparation of aromatic acetamides, i.e., acetanilides, as described in Examples 8–16 below. The advantageous feature of selective ether cleavage at the nitrogen substituent rather than on the anilide ring by hydrogen halide is shown in Examples 8–10.

EXAMPLE 8

N-(methoxymethyl)-2'-(methoxymethyl)-6'-methyl-2-chloroacetanilide (0.6 g) were dissolved in 10 ml $CCl_4$ and shaken with 10 ml 37% HCl; the layers were separated and Nmr indicated complete reaction. However, to assure complete reaction, an additional 10 ml of 37% HCl were added and the mixture shaken. The layers were again separated and the organic layer stripped to give 0.3 g of an oil.

| Anal. calc'd for $C_{12}H_{15}Cl_2NO_2$ (%): | | |
| --- | --- | --- |
| Element | Theory | Found |
| C | 52.19 | 50.82 |
| H | 5.47 | 5.68 |
| N | 5.07 | 4.78 |

Nmr: ($CDCl_3$ as solvent), chemical shifts (from TMS=O) $\delta$:2.3 ArCH$_3$ (S, 3H); $\delta$=3.35 C$\underline{H}_3$O (S, 3H); $\delta$=3,8 ClC$\underline{H}_2$CO (AB Quartet, 2H, J:12 HZ; $\delta$=4.4 AR—C$\underline{H}_2$OCH$_3$ (AB Quartet, 2H, J=10 Hz); $\delta$=5.48

ClC$\underline{\text{H}}_2$N (AB Quartet 2H, J=8 Hz). The product was identified as N-(chloromethyl)-2'-(methoxymethyl)-6'-methyl-2-chloroacetanilide.

EXAMPLE 9

To a solution of 9.6 g CH$_3$OH and 4.5 g of paraformaldehyde in about 250 ml CH$_2$Cl$_2$, cooled in an ice-water bath, was added 11.8 g acetyl chloride in about one minute. The reaction mixture was stirred for 1.5 hours, then 9.3 g of 2'-methoxy-6'-methyl-2-chloroacetanilide and 5.0 g of triethylbenzyl ammonium chloride were added. After stirring for 5.0 minutes, 50 ml of 50% NaOH were carefully added over about 0.5 minute. The reaction mixture was stirred for 0.5 hour; examination by GLC indicated the reaction to be essentially complete. To the mixture was added 150 ml water, shaken and the formed layers separated. The organic layer was washed with 150 ml water, then 150 ml of saturated NaCl. The organic layer was dried over MgSO$_4$, then filtered to give a crude oil. Upon Kugelrohr distillation, b.p. 145° C./0.15 mm, 10.07 g (90% yield) of clear oil was obtained. Nmr confirmed structure as N-(methoxymethyl)-2'-methoxy-6'-methyl-2-chloroacetanilide.

The above-prepared product was taken up in 100 ml of CCl$_4$, then 100 ml of concentrated HCl added. The mixture was stirred for 0.5 hour, during which time a solid product formed. Fifty ml of water and 50 ml of CH$_2$Cl$_2$ were added. The organic layer was extracted, washed with 100 ml water, then 100 ml of saturated NaCl, then dried over MgSO$_4$, concentrated, then vacuum treated to give 9.62 g (94% yield) of white solid product identified as N-(chloromethyl)-2'-methoxy-6'-methyl-2-chloroacetanilide, m.p. 105° C.

EXAMPLE 10

A suspension of 3.80 g of N-(methoxymethyl)-2',6'-dimethoxy-2-chloroacetanilide (prepared by said N-alkylation process) in 40 ml of CCl$_4$ was stirred with 40 ml of conc. HCl for 15 minutes. The mixture was transferred to a separatory funnel, to which was added 100 ml CHCl$_2$. The organic layer was separated, washed twice with 100 ml water, then 100 ml of saturated NaCl. The organic layer was then dried with MgSO$_4$, filtered and concentrated to give 3.80 g (97.0%) of a solid product identified as N-(chloromethyl)-2',6'-dimethoxy-2-chloroacetanilide, m.p. 95°-97° C.

EXAMPLE 11

N-(methoxymethyl)-2'-(trifluoromethyl)-6'-methyl-2-chloroacetanilide, 12.8 g (0.043 mol), was dissolved in about 100 ml of CCl$_4$ and mixed with about 200 ml of 37% HCl. The reaction mixture was stirred in an oil bath heated to 40°-45° C. for 1.0 hour. GLC and Nmr analysis indicated almost complete reaction. The layers were separated after 1.5 hours and the organic layer dried over MgSO$_4$, filtered and stripped. A sample of the product was distilled by Kugelrohr to give 10.0 g (77% yield) of yellow oil, N$_D^{25}$ 1.5076.

| Anal. calc'd for C$_{11}$H$_{10}$Cl$_2$F$_3$NO (%): | | |
|---|---|---|
| Element | Theory | Found |
| C | 44.02 | 44.82 |
| H | 3.36 | 3.43 |
| N | 4.67 | 4.74 |

The product was identified as N-(chloromethyl)-2'-(trifluoromethyl)-6'-methyl-2-chloroacetanilide.

EXAMPLE 12

Following substantially the same procedure described in Example 11, there is prepared N-(chloromethyl)-2'-(trifluoromethyl)-6'-ethyl-2-chloroacetanilide, a white solid m.p. 46°-50° C.

| Anal. calc'd for C$_{12}$H$_{12}$Cl$_2$F$_3$NO (%): | | |
|---|---|---|
| Element | Theory | Found |
| C | 45.88 | 45.89 |
| H | 3.85 | 4.45 |
| N | 4.46 | 4.45 |

EXAMPLE 13

N-(Methoxymethyl)-2'-(trifluoromethyl)-2-chloroacetanilide (12.6 g) dissolved in 125 ml CCl$_4$ and agitated with 200 ml 37% HCl. Reaction was complete in one hour; layers were separated, dried, filtered and stripped. Residue from ether hexane crystallized. Scale-up from 67 g gave 52 g white crystals, m.p. 63°-65° C.

| Anal. calc'd for C$_{10}$H$_8$Cl$_2$F$_3$NO (%): | | |
|---|---|---|
| Element | Theory | Found |
| C | 41.98 | 41.82 |
| H | 2.82 | 2.65 |
| N | 4.90 | 4.91 |

The product was identified as N-(chloromethyl)-2'-(trifluoromethyl)-2-chloroacetanilide.

EXAMPLE 14

Ten (10.0) g of N-(methoxymethyl)-2',6'-diethyl-2-chloroacetanilide (common name "alachlor") in 100 ml of CCl$_4$ were shaken with 50 ml of 48% HBr. The mixture was stirred for about 8.0 hours and permitted to stand overnight. Nmr analysis indicated about 80% reaction. A fresh charge of 10 ml of 48% HBr were added with stirring. The layers were separated and the organic layer further stirred to give 10.2 g of oil.

| Anal. calc'd for C$_{13}$H$_{17}$BrClNO (%): | | |
|---|---|---|
| Element | Theory | Found |
| C | 49.00 | 49.69 |
| H | 5.38 | 5.52 |
| N | 4.40 | 4.38 |

The product was identified as N-(bromomethyl)-2',6'-diethyl-2-chloroacetanilide.

EXAMPLE 15

Following substantially the same procedure as described in Example 14, but substituting 37% HCl, there was obtained 9.8 g of lemon-yellow oil which was taken up in hexane and recrystallized to give a product having a melting point of 37°-38° C. Nmr and melting point confirmed structure of compound as N-(chloromethyl)-2',6'-diethyl-2-chloroacetanilide.

EXAMPLE 16

To 9.4 g of 2',6'-dimethyl-2-chloroacetanilide were added 10 ml of chloromethyl ethyl ether, 3.0 g triethylbenzyl ammonium bromide in 175 ml of CH$_2$Cl$_2$ and 100 ml of 50% NaOH with stirring and cooling; after 1.5 hours, ice was added to about 450 ml total volume. The mixture was allowed to stand overnight. GLC showed essentially only N-(ethoxymethyl)-2',6'-dimethyl-2-chloroacetanilide. On workup (water wash, MgSO$_4$ drying, vacuum stripping), there was obtained 12.3 g of product (some mechanical loss occurred).

To the 12.3 g of the above product were mixed 60 ml of 37% HCl and 20 ml of CCl$_4$; the mixture was stirred about 4.0 hours, then a second charge of 30 ml of 37% HCl added over 15 minutes with stirring. The layers were separated and 9.0 g of product recovered; colorless crystals, m.p. 94°–95° C.

| Anal. calc'd for C$_{11}$H$_{13}$Cl$_2$NO (%): | | |
|---|---|---|
| Element | Theory | Found |
| C | 53.7 | 53.8 |
| H | 5.3 | 5.5 |
| N | 28.8 | 29.0 |

The product was identified as N-(chloromethyl)-2',6'-dimethyl-2-chloroacetanilide.

As indicated above, the N-(halomethyl) acylamide compounds prepared according to the process of this invention are generally known compounds, some of which have herbicidal activity themselves. All of the N-halomethyl compounds disclosed above have utility as intermediate compounds (precursors) in the preparation of other compounds having herbicidal activity as disclosed, e.g., in the references cited above. Additionally, the N-(halomethyl)-2-chloroacetamides prepared in accordance with Examples 1 and 2 above are useful in the preparation of novel N-(azolylmethyl)-2-haloacetamides as set forth in this inventor's co-pending application Ser. No. 211,609, filed of even date herewith. Examples 17–19 below are illustrative of the preparation of said novel 2-haloacetamides.

EXAMPLE 17

To 1.4 g (0.0059 mol) of the N-(chloromethyl)-2-chloroacetamide prepared in Example 1 above was added 0.8 g (0.012 mol) of pyrazole and the mixture heated in about 20 ml of toluene at 80°–90° C. for about 6–7 hours. The material was decanted, washed with 10% caustic then with water, stripped and recrystallized from methylcyclohexane to give 1.0 (63% yield) of white solid, m.p. 101.0°–101.5° C.

| Anal. calc'd for C$_{13}$H$_{20}$ClN$_3$O (%): | | |
|---|---|---|
| Element | Theory | Found |
| C | 57.88 | 57.41 |
| H | 7.47 | 7.59 |
| N | 15.58 | 16.25 |

The product, structure confirmed by Nmr, was identified as N-[(2-methyl-1-(1-methylethyl)-1-propen-1-yl]-N-(1H-pyrazol-1-ylmethyl)-2-chloroacetamide.

EXAMPLE 18

Pyrazol, 0.54 g (0.008 mol) and 0.8 g (0.0038 mol) of the N-(chloromethyl)-2-chloroacetamide prepared in Example 2 above were mixed in toluene and heated at 90° C. On work-up as described in Example 14, 0.6 g (62% yield) of an amber oil was obtained.

| Anal. calc'd for C$_{11}$H$_{16}$ClN$_3$O (%): | | |
|---|---|---|
| Element | Theory | Found |
| C | 54.66 | 54.71 |
| H | 6.67 | 6.80 |
| N | 17.38 | 17.51 |

The product, confirmed by Nmr, was identified as N-(1,2-dimethyl-1-propen-1-yl)-N-(1H-pyrazol-1-ylmethyl)-2-chloroacetamide.

EXAMPLE 19

To 8.9 g (0.036 mol) of the amide produced in Example 4(b) dissolved in toluene was added 4.9 g (0.072 mol) of pyrazole; this mixture was heated to 90° C. with stirring for 7 hours. The following day, the toluene solution was decanted, washed twice with water, then vacuum distilled to remove the solvent and traces of moisture. The residue was 9.0 g of an oil which crystallized on standing. A sample of the product was recrystallized from a heptane/methylcyclohexane solvent to give a solid product, m.p. 83°–84° C., in 89% yield.

| Anal. calc'd for C$_{14}$H$_{20}$ClN$_3$O (%): | | |
|---|---|---|
| Element | Theory | Found |
| C | 59.67 | 59.64 |
| H | 7.15 | 7.17 |
| N | 14.91 | 14.96 |

The product was identified as N-(2,6-dimethyl-1-cyclohexen-1-yl)-N-(1H-pyrazol-1-ylmethyl)-2-chloroacetamide.

EXAMPLE 20

This example describes the use of an N-(halomethyl)-substituted-2-haloacetanilide to prepare other novel N-heteromethyl-2-haloacetanilides as disclosed and claimed in this inventor's co-pending application, Ser. No. 133,763, filed Mar. 25, 1980.

N-(chloromethyl)-2'-methoxy-6'-methyl-2-chloroacetanilide 3.6 g (0.0137 mol), in 100 ml of CH$_2$Cl$_2$ were mixed with benzothiazolin-2-one, 2.2 g (0.0145 mol) and 1.0 benzyl triethyl ammonium bromide. To this mixture with stirring was added 30 ml of 50% caustic; the mixture was allowed to react for about three hours. On work-up 5.8 g crude product was isolated, then recrystallized from isopropanol to a light buff-colored solid, m.p. 120°–121° C.

| Anal. calc'd for C$_{18}$H$_{17}$ClN$_2$O$_3$S (%): | | |
|---|---|---|
| Element | Theory | Found |
| C | 57.37 | 56.89 |
| H | 4.55 | 4.51 |
| N | 7.43 | 7.34 |

The product was identified as N-(2'-methoxy-6'-methyl)-N-[(2-oxo-3(2H)-benzothiazolyl)methyl]-2-chloroacetanilide.

The process of this invention is of wide applicability as indicated in the above working embodiments. Still further, the process of this invention may be suitably used to prepare a variety of other 2-haloacetamides from the appropriate N-halomethyl starting material. Since the reactive site in the halogen-ether cleavage process is at the N-methylene ether position, a wide variety of substituents may occupy the other non-haloacetyl position in the amide. That is, in Formula II herein, in addition to the R members exemplified above, other R members are within the purview of this invention. Thus, R may be hydrogen, aliphatic, cycloaliphatic, heterocyclic or aromatic members, including alkyl, alkenyl, alkynyl, cycloalkyl, alkylcycloalkyl, all preferably having up to 6 carbon atoms, N-, O-, or S-heterocyclic radicals, which members may be independently substituted with non-interfering radicals, e.g., alkyl, halogen, nitro, $CF_3$, alkoxy, polyalkoxy, alkoxyalkyl and the like. A subgenus of N-halomethyl compounds of particular interest is that wherein the R group is a phenyl radical substituted in one ortho position with a $C_{1-4}$ alkyl radical and in the other ortho position with a $C_{1-4}$ alkoxy or $C_{3-4}$ alkenyloxy radical. Exemplary of such compounds are the following:

N-(chloromethyl)-2'-methoxy-6'-methyl-2-chloroacetanilide

N-(chloromethyl)-2'-isopropoxy-6'-methyl-2-chloroacetanilide

N-(chloromethyl)-2'-isobutoxy-6'-methyl-2-chloroacetanilide

N-(chloromethyl)-2'-n-butoxy-6'-ethyl-2-chloroacetanilide

N-(chloromethyl)-2'-(1-propen-3-yloxy)-6'-methyl-2-chloroacetanilide

Another subclass of interest is that wherein R in the above formulae is a $C_{5-7}$ 1-cycloalken-1-yl group, e.g., N-(chloromethyl)-N-(2,5-dimethyl-1-cyclopenten-1-yl)-2-chloroacetamide.

In addition to N-(halomethyl)-2-haloacetamides, other acetamides having non-halogen substituents in the 2- or α-position which may be prepared according to the process of this invention, include those wherein X in Formulae I and II above may be hydrogen, a $C_{1-6}$ alkyl or haloalkyl radical, a $C_{3-7}$ cycloalkyl radical, a phenyl or benzyl radical or any of said radicals optionally substituted with other radicals which are inert to a hydrogen halide, e.g., halogen, $NO_2$, $CF_3$, $C_{1-6}$ alkyl or alkoxy, phenyl, benzyl, etc.

Suitable solvents which may be used herein include aliphatic and aromatic hydrocarbons or halogenated hydrocarbons such as naphtha, the halogenated alkanes and alkenes, e.g., $CCl_4$, $CHCl_3$, ethylene dichloride, trichloroethane, etc., benzene, halogenated benzenes, toluene, the xylenes and other inert solvents.

It will be appreciated by those skilled in the art that the process of this invention may be modified in non-inventive modes by those skilled in the art having particular reference to the nature and ratio of reactants, particular species with the defined genus of reactants, catalysts, solvents, reaction temperatures, times, pressures, etc.

I claim:

1. Process for preparing compounds of Formula I

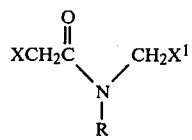

which comprises reacting a hydrogen halide with a compound of Formula II

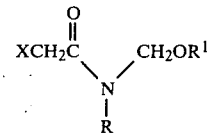

where in the above formulae

X is hydrogen, halogen, a $C_{1-6}$ alkyl or haloalkyl radical, a $C_{3-7}$ cycloalkyl radical, a phenyl or benzyl radical or any of said radicals substituted with halogen, $NO_2$, $CF_3$, $C_{1-6}$ alkyl or alkoxy, phenyl or benzyl;

$X^1$ is chloro, bromo or iodo;

R is an acyclic 1-alken-1-yl radical having up to 10 carbon atoms, a $C_{5-7}$ 1-cycloalken-1-yl radical, a phenyl radical or said 1-cycloalken-1-yl or phenyl radicals substituted with one or more $C_{1-6}$ alkyl, alkoxy or alkoxyalkyl, $C_{2-4}$ alkenyl or $C_{3-4}$ alkenyloxy, $NO_2$ or trifluoromethyl radicals or halogen, and $R^1$ is a hydrocarbyl radical having up to 10 carbon atoms or such radical substituted with halogen or $C_{1-8}$ alkoxy or alkoxyalkyl groups.

2. Process according to claim 1 wherein X and $X^1$ are chloro atoms.

3. Process according to claim 2 wherein R is an acyclic 1-alken-1-yl radical having up to 10 carbon atoms.

4. Process according to claim 3 wherein said compound of Formula I is N-(chloromethyl)-N-[2-methyl-1-(1-methylethyl)-1-propenyl]-2-chloroacetamide.

5. Process according to claim 3 wherein said compound of Formula I is N-(chloromethyl)-N-(1,2-dimethyl-1-propenyl)-2-chloroacetamide.

6. Process according to claim 2 wherein R is a $C_{5-7}$ 1-cycloalken-1-yl radical, optionally substituted with one or more $C_{1-6}$ alkyl radicals.

7. Process according to claim 6 wherein said compound of Formula I is N-(chloromethyl)-N-(2,6-dimethyl-1-cyclohexen-1-yl)-2-chloroacetamide.

8. Process according to claim 2 wherein R is a phenyl radical, optionally substituted with one or more $C_{1-6}$ alkyl, alkoxy or alkoxyalkyl, $C_{2-4}$ alkenyl or $C_{3-4}$ alkenyloxy or trifluoromethyl radicals or halogen.

9. Process according to claim 8 wherein R is a phenyl radical substituted in both ortho positions with $C_{1-6}$ alkyl radicals.

10. Process according to claim 9 wherein said compound of Formula I is N-(chloromethyl)-2',6'-diethyl-2-chloroacetanilide.

11. Process according to claim 9 wherein said compound of Formula I is N-(chloromethyl)-2'-methyl-6'-ethyl-2-chloroacetanilide.

12. Process according to claim 8 wherein R is a phenyl radical substituted in one ortho position with a $C_{1-6}$ alkyl radical and in the other ortho position with a trifluoromethyl radical.

13. Process according to claim 12 wherein said compound of Formula I is N-(chloromethyl)-2'-(trifluoromethyl)-6'-methyl-2-chloroacetanilide.

14. Process according to claim 12 wherein said compound of Formula I is N-(chloromethyl)-2'-(trifluoromethyl)-6'-ethyl-2-chloroacetanilide.

15. Process according to claim 8 wherein R is a phenyl radical substituted in one ortho position with a $C_{1-6}$ alkyl radical and in the other ortho position with a $C_{1-6}$ alkoxy or $C_{3-4}$ alkenyloxy radical.

16. Process according to claim 15 wherein said alkyl radical is methyl or ethyl.

17. Process according to claim 16 wherein said alkoxy radical is a methoxy or $C_3$ or $C_4$ alkoxy radical.

18. Process according to claim 17 wherein said compound of Formula I is N-(chloromethyl)-2'-methoxy-6'-methyl-2-chloroacetanilide.

19. Process according to claim 17 wherein said compound of Formula I is N-(chloromethyl)-2'-isopropoxy-6'-methyl-2-chloroacetanilide.

20. Process according to claim 17 wherein said compound of Formula I is N-(chloromethyl)-2'-isobutoxy-6'-methyl-2-chloroacetanilide.

21. Process according to claim 17 wherein said compound of Formula I is N-(chloromethyl)-2'-isobutoxy-6'-ethyl-2-chloroacetanilide.

22. Process according to claim 17 wherein said compound of Formula I is N-(chloromethyl)-2'-n-butoxy-6'-ethyl-2-chloroacetanilide.

23. Process according to claim 16 wherein said other ortho position is occupied by a $C_{3-4}$ alkenyloxy radical.

24. Process according to claim 23 wherein said compound of Formula I is N-(chloromethyl)-2'-(1-propen-3-yloxy)-6'-methyl-2-chloroacetanilide.

25. Process according to claim 6 wherein said compound of Formula I is N-(chloromethyl)-N-(2,5-dimethyl-1-cyclopenten-1-yl)-2-chloroacetamide.

* * * * *